US006903248B2

(12) United States Patent
Pang et al.

(10) Patent No.: US 6,903,248 B2
(45) **Date of Patent: *Jun. 7, 2005**

(54) DNA CONSTRUCTS AND METHODS TO IMPART RESISTANCE TO AT LEAST ONE VIRUS ON PLANTS

(75) Inventors: Sheng-Zhi Pang, Ellisville, MO (US); Dennis Gonsalves, Geneva, NY (US); Fuh-Jyh Jan, Ithaca, NY (US)

(73) Assignee: Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/025,635

(22) Filed: Feb. 18, 1998

(65) Prior Publication Data

US 2004/0216181 A1 Oct. 28, 2004

Related U.S. Application Data

(60) Provisional application No. 60/035,350, filed on Feb. 19, 1997, and provisional application No. 60/062,870, filed on Oct. 21, 1997.

(51) Int. Cl.[7] ........................... A01H 5/00; A01H 5/10; C12N 15/82

(52) U.S. Cl. .................... 800/301; 800/280; 435/320.1; 424/93.2; 536/23.72

(58) Field of Search ................................ 800/280, 301, 800/279, 278, 298, 290, 295; 435/320.1, 418, 419, 69.1, 468, 410; 424/93.2; 536/23.72; 530/23.1, 23.4, 23.2, 23.6, 23.72, 24.1, 24.2

(56) References Cited

U.S. PATENT DOCUMENTS

| | | | | |
|---|---|---|---|---|
| 4,818,689 | A | 4/1989 | Suciu-Foca et al. | |
| 5,034,323 | A | 7/1991 | Jorgensen et al. | 800/282 |
| 5,175,102 | A | 12/1992 | Baulcombe et al. | 800/279 |
| 5,231,020 | A | 7/1993 | Jorgensen et al. | 800/281 |
| 5,254,802 | A | 10/1993 | Hoekstra et al. | |
| 5,283,184 | A | 2/1994 | Jorgensen et al. | 800/285 |
| 5,292,362 | A | 3/1994 | Bass et al. | |
| 5,405,750 | A | 4/1995 | Suciu-Foca et al. | |
| 5,491,084 | A | 2/1996 | Chalfie et al. | |
| 5,530,196 | A | 6/1996 | Fraley et al. | 800/298 |
| 5,569,823 | A | 10/1996 | Schreier et al. | |
| 5,571,706 | A | 11/1996 | Baker et al. | 800/279 |
| 5,576,202 | A | 11/1996 | Pehu et al. | 800/280 |
| 5,583,021 | A | 12/1996 | Dougherty et al. | 800/280 |
| 5,589,612 | A | 12/1996 | Jilka et al. | 800/280 |
| 5,589,625 | A | 12/1996 | Saarma et al. | 800/279 |
| 5,741,668 | A | 4/1998 | Ward et al. | |
| 5,773,700 | A | 6/1998 | Van Grinsven et al. | |
| 5,998,699 | A | 12/1999 | Slightom et al. | |
| 6,002,072 | A | 12/1999 | McMaster et al. | |

FOREIGN PATENT DOCUMENTS

| | | | |
|---|---|---|---|
| WO | WO 94/16550 | * | 8/1994 |
| WO | WO 96/21019 | | 7/1996 |
| WO | 96/210031 | * | 7/1996 |

OTHER PUBLICATIONS van der Krol et al., Inhibition of flower pigmentation by antisense CHS gene; promoter and minimal sequance requirements for the antisense effect, 1990, Plant Molecular Biology, vol. 14, pp. 457–466.*

Blokland et al., Transgene–mediated suppression of chalcone synthase expression in *Petunia hydrida* results from an increase in RNA turnover, 1994, The Plant Journal, vol. 6, No. 6, pp. 861–877.*

Jan et al., A minimum length of N gene sequence in transgenic plants is required for RNA–mediated tospovirus resistance, 2000, Journal of General Virology, vol. 81, pp. 235–242.*

Lawson et al., Engineering resistance to mixed virus infection in a commercial potato cultivar: resistance to potato . . . , Feb. 1990, Bio/technology, vol. 8, pp. 127–134.*

Seymour et al. Plant Molecular Biology. 1993. vol. 23: 1–9, 1993.*

Cai et al., "A Protocol For Efficient Transformation and Regeneration of *Carica papaya* L.," *Plant* 35:61–69 (1999).

Fitch et al., "Virus Resistant Papaya Plants Derived from Tissues Bombarded with the Coat Protein Gene of Papaya Ringspot Virus," *Bio/Technology* 10:1466–1472 (1992).

Tennant et al., "Differential Protection Against Papaya Ringspot Virus Isolates in Coat Protein Gene Transgenic Papaya and Classically Cross–Protected Papaya," *The American Phytopathological Society* 84(11):1359–1366 (1994).

Chuang et al., "Specific and Heritable Genetic Interference by Double–Stranded RNA in *Arabidopsis thaliana,*" *PNAS* 97(9):4985–4990 (2000).

Levin et al., Methods of Double–Stranded RNA–Mediated Gene Inactivation in *Arabidopsis* and Their Use to Define an Essential Gene in Methionine Biosynthesis, *Plant Molecular Biology* 44:759–775 (2000).

(Continued)

*Primary Examiner*—Anne Kubelik
(74) *Attorney, Agent, or Firm*—Nixon Peabody LLP

(57) ABSTRACT

The present invention is directed to a DNA construct comprising a first DNA molecule having a length insufficient to independently impart resistance to a virus to plants transformed with said first DNA molecule, wherein the first DNA molecule is from a viral coat protein gene and is at least 110 nucleotides in length. The construct also comprises a second DNA of at least 400 nucleotides in length, which is coupled to the first DNA molecule so that the first and second DNA molecules collectively achieve post-transcriptional silencing and impart resistance to the virus. Alternately, the DNA construct can comprise a plurality of DNA molecules each of which is at least 110 nucleotides in length and from a viral gene, wherein the plurality of DNA molecules are at least 510 nucleotides in length.

18 Claims, 7 Drawing Sheets

OTHER PUBLICATIONS

Smith et al., "Transgenic Plant Virus Resistance Mediated by Untranslatable Sense RNAs: Expression, Regulation, and Fate of Nonessential RNAs," *The Plant Cell* 6:1441–1453 (1994).

Senior, "Uses of Plant Gene Silencing," *Biotechnology and Genetic Engineering Reviews* 15:79–119 (1998).

Pang et al., "Resistance to Heterologous Isolates of Tomato Spotted Wilt Virus in Transgenic Tobacco Expressing Its Nucleocapsid Protein Gene," *Mol. Plant Pathology* 82(10):1223–1229 (1992).

Pang et al., "Different Mechanisms Protect Transgenic Tobacco Against Tomato Spotted Wilt Virus and Impatiens Necrotic Spot Tospoviruses," *Bio/Technology* 11(7):819–824 (1993).

Gonsalves et al., "Developing Transgenic Crops That Are Resistant to Tospoviruses," *Acta Horticulturae* 431:427–431 (1997).

Pang et al., "Post–Transcriptional Transgene Silencing and Consequent Tospovirus Resistance in Transgenic Lettuce are Affected By Transgene Dosage and Plant Development," *The Plant Journal* 9(6):899–909 (1996).

Epel et al., "Plant Virus Movement Protein Dynamics Probed with a GFP–Protein Fusion," *Gene* 173:75–79 (1996).

Seymour, G.B., et al., "Down–Regulation of Two Non–Homologous Endogenous Tomato Genes With a Single Chimeric Sense Gene Construct," *Plant Molecular Biology* 23:1–9 (1993.

Pang, S., et al., "The Biological Properties of a Distinct Tospovirus and Sequence Analysis of its S RNA," *Phytopathology* 83(7):723–33 (1993).

Pang, S., et al., "Resistance of Transgenic *Nicotiana benthamiana* Plants to Tomato Spotted Wilt and Impatiens Necrotic Spot Tospoviruses: Evidence of Involvement of the N Protein and N Gene RNA in Resistance," *Phytopathology* 84(3):243–49 (1994).

Voinnet et al., "Systemic Signalling in Gene Silencing," *Nature*, 389:553 (1997).

Tanzer et al., "Characterization of Post–Transcriptionally Suppressed Transgene Expression That Confers Resistance to Tobacco Etch Virus Infection in Tobacco," *The Plant Cell*, 9:1411–1423 (1997).

Taylor, "Comprehending Cosuppression," *The Plant Cell*, 9:1245–1249 (1997).

Pang et al., "Nontarget DNA Sequences Reduce the Transgene Length Necessary for RNA–Mediated Tospovirus Resistance in Transgenic Plants," *Proc. Natl. Acad. Sci. USA*, 94:8261–8266 (1997).

Ratcliff et al., "A Similarity Between Viral Defense and Gene Silencing in Plants," *Science*, 276:1558–1563 (1997).

Jorgensen, Altered Gene Expression in Plants Due to Trans Interactions Between Homologous Genes, *TIBTECH*, 8:340–344 (1990).

Grierson et al., "Does Co–Suppression of Sense Genes in Transgenic Plants Involve Antisence RNA?," *TIBTECH*, 9:122–123 (1991).

Hellwald et al., "Viral RNA As a Potential Target for Two Independent Mechanisms of Relticase–Mediated Resistance Against Cucumber Mosaic Virus," *Cell*, 83:937–946 (1995).

Angell et al., "Consistent Gene Silencing in Transgenic Plants Expressing a Replicating Potato Virus X RNA," *EMBO Journal*, 16:3675–3684 (1997).

* cited by examiner

SEQUENCE LISTING

```
(1) GENERAL INFORMATION:

    (iii) NUMBER OF SEQUENCES: 18


(2) INFORMATION FOR SEQ ID NO:1:

    (i) SEQUENCE CHARACTERISTICS:
          (A) LENGTH: 46 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:1:

AGCTAATCTA GAACCATGGA TGACTCACTA AGGAAAGCAT TGTTGC                    46


(2) INFORMATION FOR SEQ ID NO:2:

    (i) SEQUENCE CHARACTERISTICS:
          (A) LENGTH: 38 base pairs
          (B) TYPE: nucleic acid
          (C) STRANDEDNESS: single
          (D) TOPOLOGY: linear

    (ii) MOLECULE TYPE: cDNA
```

-continued (xi) SEQUENCE DESCRIPTION: SEQ ID NO:2:

TACAGTTCTA GAACCATGGT CTGGAAAACC TTGACCAG 38

(2) INFORMATION FOR SEQ ID NO:3:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

TACAGTTCTA GAACCATGGT AAAGCGATTT TACTTTTGGT A 41

(2) INFORMATION FOR SEQ ID NO:4:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

AGATTCTCTA GACCATGGTG ACTTGATGAG CAAAGTCTGT GAGGCTTGC 49

(2) INFORMATION FOR SEQ ID NO:5:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

TACAGTTCTA GAACCATGGA AAATACAAGG ATCTCGGG 38

(2) INFORMATION FOR SEQ ID NO:6:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

TACAGTTCTA GAACCATGGT AGAAGGGGAA AGAGTATGCT G 41

(2) INFORMATION FOR SEQ ID NO:7:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

AGCATTGGAT CCATGGTTAA CACACTAAGC AAGCAC 36

-continued (2) INFORMATION FOR SEQ ID NO:8:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

TCTTGAGGAT CCATGGCTGA TCTTCATTCA TTTCAA 36

(2) INFORMATION FOR SEQ ID NO:9:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

TCTTGAGGAT CCATGGATCC TGATATATAG CCAAGA 36

(2) INFORMATION FOR SEQ ID NO:10:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

TACAGTGGAT CCATGGTTAA GGTAATCCAT AGGCTTGAC 39

(2) INFORMATION FOR SEQ ID NO:11:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

TCTTGAGGAT CCATGGCTTA ATAACCTTCA TTATGC 36

(2) INFORMATION FOR SEQ ID NO:12:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

TCTTGAGGAT CCATGGAAAA GTCTTGAAGT TGAATG 36

(2) INFORMATION FOR SEQ ID NO:13:

(i) SEQUENCE CHARACTERISTICS:

-continued (A) LENGTH: 50 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

AGCTAATCTA GAACCATGGA TGAAAAATTA CCATAAAGAA AACTTCAGAC 50

(2) INFORMATION FOR SEQ ID NO:14:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

AGCATTGGAT CCATGGTTAG TTACCTAGTT TTCTTTTCAG CACAGTGCAA ACT 53

(2) INFORMATION FOR SEQ ID NO:15:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

TTGACTCCAT GGCAGGTGAA ACGCTTGACG 30

(2) INFORMATION FOR SEQ ID NO:16:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

GTCGTACCAT GGCGAGAATA CTAACGAGTA AAC 33

(2) INFORMATION FOR SEQ ID NO:17:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

TGAACATCTA GAACCATGGG TAAAGGAGAA GAACTTTTCA CTGG 44

(2) INFORMATION FOR SEQ ID NO:18:

(i) SEQUENCE CHARACTERISTICS:
(A) LENGTH: 44 base pairs
(B) TYPE: nucleic acid
(C) STRANDEDNESS: single
(D) TOPOLOGY: linear -continued

```
(ii) MOLECULE TYPE: cDNA

(xi) SEQUENCE DESCRIPTION: SEQ ID NO:18:

TGAACAGGAT CCATGGTCTA CGAATGCTAT TATTTGTATA GTTC                    44
```

DNA CONSTRUCTS AND METHODS TO IMPART RESISTANCE TO AT LEAST ONE VIRUS ON PLANTS

FIELD OF THE INVENTION

This application claims the benefit of U.S. Provisional Application Ser. Nos. 60/035,350 filed Feb. 19, 1997 and 60/062,870 filed Oct. 21, 1997.

The present invention is directed to a DNA construct to confer multiple traits on plants.

BACKGROUND OF THE INVENTION

Control of plant virus diseases took a major step forward in the last decade when it was shown in 1986 that the tobacco mosaic virus ("TMV") coat protein gene that was expressed in transgenic tobacco conferred resistance to TMV (Powell-Abel, P., et al., "Delay of Disease Development in Transgenic Plants that Express the Tobacco Mosaic Virus Coat Protein Gene," *Science,* 232:738–43 (1986)). The concept of pathogen-derived resistance ("PDR"), which states that pathogen genes that are expressed in transgenic plants will confer resistance to infection by the homologous or related pathogens (Sanford, J. C., et al. "The Concept of Parasite-Derived Resistance—Deriving Resistance Genes from the Parasite's Own Genome," *J. Theor. Biol.,* 113:395–405 (1985)) was introduced at about the same time. Since then, numerous reports have confirmed that PDR is a useful strategy for developing transgenic plants that are resistant to many different viruses (Lomonossoff, G. P., "Pathogen-Derived Resistance to Plant Viruses," *Ann. Rev. Photopathol.,* 33:323–43 (1995)).

Only eight years after the report by Beachy and colleagues (Powell-Abel, P., et al., "Delay of Disease Development in Transgenic Plants that Express the Tobacco Mosaic Virus Coat Protein Gene," *Science,* 232:738–43 (1986)), Grumet, R., "Development of Virus Resistant Plants via Genetic Engineering," *Plant Breeding Reviews,* 12:47–49 (1994) reviewed the PDR literature and listed the successful development of virus resistant transgenic plants to at least 11 different groups of plant viruses. The vast majority of reports have utilized the coat protein genes of the viruses that are targeted for control. Although the testing of transgenic plants have been largely confined to laboratory and greenhouse experiments, a growing number of reports showed that resistance is effective under field conditions (e.g., Grumet, R., "Development of Virus Resistant Plants via Genetic Engineering," *Plant Breeding Reviews,* 12:47–49 (1994)). Two virus resistant crops have been deregulated by APHIS/USDA and thus are approved for unrestricted release into the environment in the U.S.A. Squash that are resistant to watermelon mosaic virus 2 and zucchini yellow mosaic potyviruses have been commercialized (Fuchs, M., et al., "Resistance of Transgenic Hybrid Squash ZW-20 Expressing the Coat Protein Genes of Zucchini Yellow Mosaic Virus and Watermelon Mosaic Virus 2 to Mixed Infections by Both Potyviruses," *Bio/Technology,* 13:1466–73 (1995); Tricoli, D. M., et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus," *Bio/Technology,* 13:1458–65 (1995)). Also, a transgenic papaya that is resistant to papaya ringspot virus has been developed (Fitch, M. M. M., et al., "Virus Resistant Papaya Derived from Tissues Bombarded with the Coat Protein Gene of Papaya Ringspot Virus," *Bio/Technology,* 10:1466–72 (1992); Tennant, P. F., et al., "Differential Protection Against Papaya Ringspot Virus Isolates in Coat Protein Gene Transgenic Papaya and Classically Cross-Protected Papaya," *Phytopathology,* 84:1359–66 (1994)). This resistant transgenic papaya was recently deregulated by USDA/APHIS. Deregulation of the transgenic papaya is timely, because Hawaii's papaya industry is being devastated by papaya ringspot virus. Undoubtedly, more crops will be deregulated and commercialized in the near future.

Interestingly, remarkable progress has been made in developing virus resistant transgenic plants despite a poor understanding of the mechanisms involved in the various forms of pathogen-derived resistance (Lomonossoff, G. P., "Pathogen-Derived Resistance to Plant Viruses," *Ann. Rev. Photopathol.,* 33:323–43 (1995)). Although most reports deal with the use of coat protein genes to confer resistance, a growing number of reports have shown that viral replicase (Golemboski, D. B., et al., "Plants Transformed with a Tobacco Mosaic Virus Nonstructural Gene Sequence are Resistant to the Virus," *Proc. Natl. Acad. Sci. USA,* 87:6311–15 (1990)), movement protein (e.g., Beck, D. L., et al., "Disruption of Virus Movement Confers Broad-Spectrum Resistance Against Systemic Infection by Plant Viruses with a Triple Gene Block," *Proc. Natl. Acad. Sci. USA,* 91:10310–14 (1994)), NIa proteases of potyviruses (e.g., Maiti, I. B., et al., "Plants that Express a Potyvirus Proteinase Gene are Resistant to Virus Infection," *Proc. Natl. Acad. Sci. USA,* 90:6110–14 (1993)), and other viral genes are effective. This led to the conclusion that any part of a plant viral genome gives rise to PDR. Furthermore, the viral genes can be effective in the translatable and nontranslatable sense forms, and less frequently antisense forms (e.g., Baulcombe, D. C., "Mechanisms of Pathogen-Derived Resistance to Viruses in Transgenic Plants," *Plant Cell,* 8:1833–44 (1996); Dougherty, W. G., et al., "Transgenes and Gene Suppression: Telling us Something New?," *Current Opinion in Cell Biology,* 7:399–05 (1995); Lomonossoff, G. P., "Pathogen-Derived Resistance to Plant Viruses," *Ann. Rev. Photopathol.,* 33:323–43 (1995)).

RNA-mediated resistance is the form of PDR where there is clear evidence that viral proteins do not play a role in conferring resistance to the transgenic plant. The first clear cases for RNA-mediated resistance were reported in 1992 for tobacco etch ("TEV") potyvirus (Lindbo, et al., "Pathogen-Derived Resistance to a Potyvirus Immune and Resistance Phenotypes in Transgenic Tobacco Expressing Altered Forms of a Potyvirus Coat Protein Nucleotide Sequence," *Mol. Plant Microbe Interact.,* 5:144–53 (1992)), for potato virus Y ("PVY") potyvirus by Van Der Vlugt, R. A. A., et al., "Evidence for Sense RNA-Mediated Protection to PVY in Tobacco Plants Transformed with the Viral Oat Protein Cistron," *Plant Mol. Biol.,* 20:631–39 (1992), and for tomato spotted wilt ("TSWV") tospovirus by de Haan, P., et al., "Characterization of RNA-Mediated Resistance to Tomato Spotted Wilt Virus in Transgenic Tobacco Plants," *Bio/Technology,* 10:1133–37 (1992). Others confirmed the occurrence of RNA-mediated resistance with potyviruses (Smith, H. A., et al., "Transgenic Plant Virus Resistance Mediated by Untranslatable Sense RNAs: Expression, Regulation, and Fate of Nonessential RNAs," *Plant Cell,* 6:1441–53 (1994)), potexviruses (Mueller, E., et al., "Homology-Dependent Resistance: Transgenic Virus Resistance in Plants Related to Homology-Dependent Gene Silencing," *Plant Journal,* 7:1001–13 (1995)), and TSWV and other topsoviruses (Pang, S. Z., et al., "Resistance of Transgenic Nicotiana Benthamiana Plants to Tomato Spotted Wilt and Impatiens Necrotic Spot Tospoviruses: Evidence of Involvement of the N Protein and N Gene RNA in Resistance," *Phytopathology,* 84:243–49 (1994); Pang, S.-Z., et al., "Different Mechanisms Protect Transgenic Tobacco Against Tomato Spotted Wilt Virus and Impatiens Necrotic Spot Tospoviruses," *Bio/Technology* 11:819–24 (1993)). More recent work has shown that RNA-mediated resistance also occurs with the comovirus cowpea mosaic virus (Sijen, T., et al., "RNA-Mediated Virus Resistance: Role of Repeated Transgene and Delineation of Targeted Regions," *Plant Cell,* 8:2227–94 (1996)) and squash mosaic virus (Jan, F.-J., et al., "Genetic and Molecular Analysis of Squash Plants Transformed with Coat Protein Genes of Squash Mosaic Virus," *Phytopathology,* 86:S16–17 (1996)).

Major advances towards understanding the mechanism(s) of RNA-mediated resistance were made by Dougherty and colleagues in a series of experiments with TEV and PVY. Using TEV, Lindbo, J. A., "Pathogen-Derived Resistance to a Potyvirus Immune and Resistant Phenotypes in Transgenic Tobacco Expressing Altered Forms of a Potyvirus Coat Protein Nucleotide Sequence," *Mol. Plant Microbe Interact.,* 5:144–53 (1992) and Lindbo, J. A., et al., "Untranslatable Transcripts of the Tobacco Etch Virus Coat Protein Gene Sequence can Interfere with Tobacco Etch Virus Replication in Transgenic Plants and Protoplasts," *Virology,* 189:725–33 (1992) showed that transgenic plants expressing translatable full length coat protein, truncated translatable coat protein, antisense coat protein genes, and nontranslatable coat protein gene had various phenotypic reactions after inoculation with TEV. Transgenic plants displayed resistance, recovery (inoculated plants initially show systemic infection but younger leaves that develop later are symptomless and resistant to the virus), or susceptible phenotypes. Furthermore, they showed that leaves of resistant plants and asymptomatic leaves of recovered plants had relatively low levels of steady state RNA when compared to those in leaves of susceptible plants (Lindbo, J. A., et al., "Induction of a Highly Specific Antiviral State in Transgenic Plants: Implications for Regulation of Gene Expression and Virus Resistance," *Plant Cell,* 5:1749–59 (1993)). However, nuclear run off experiments showed that those plants with low levels of steady state RNA had higher transcription rates of the viral transgene than those plants that were susceptible (and had high steady state RNA levels). To account for these observations, it was proposed "that the resistant state and reduced steady state levels of transgene transcript accumulation are mediated at the cellular level by a cytoplasmic activity that targets specific RNA sequences for inactivation" (Lindbo, J. A., et al., "Induction of a Highly Specific Antiviral State in Transgenic Plants: Implications for Regulation of Gene Expression and Virus Resistance," *Plant Cell,* 5:1749–59 (1993)). It was also suggested that the low steady state RNA levels may be due to post-transcriptional gene silencing, a phenomenon that was first proposed by de Carvalho, F., et al., "Suppression of beta-1,3-glucanase Transgene Expression in Homozygous Plants," *EMBO J.,* 11:2595–602 (1992) for the suppression of β-1,3-glucanase transgene in homozygous transgenic plants.

An RNA threshold model was proposed to account for the observations (Lindbo, J. A., et al., "Induction of a Highly Specific Antiviral State in Transgenic Plants: Implications for Regulation of Gene Expression and Virus Resistance," *Plant Cell,* 5:1749–59 (1993)). Basically, the model states that there is a cytoplasmic cellular degradation mechanism that acts to limit the RNA levels in plant cells, and that this mechanism is activated when the transgenic RNA transcript goes above a threshold level. The degradation mechanism is specific for the transcript that goes above the threshold level; and if the transcripts that go above a certain threshold is a viral transgene, the virus resistance state is observed in the plant, because the degradation mechanism also targets, for inactivation, the specific sequences of the incoming virus. The model also accounts for the 'recovery' of transgenic plants by suggesting that viral RNA from the systemically invading virus triggers the phenomenon in some transgenic plants that have two copies of the transgenes. Plants that had more than three copies of the transgenes caused the threshold level to be surpassed without the invasion of virus (Goodwin, J., et al., "Genetic and Biochemical Dissection of Transgenic RNA-Mediated Virus Resistance," *Plant Cell,* 8:95–105 (1996); Smith, H. A., et al., "Transgenic Plant Virus Resistance Mediated by Untranslatable Sense RNAs: Expression, Regulation, and Fate of Nonessential RNAs," *Plant Cell,* 6:1441–53 (1994)). Although the degradation mechanism is not clear, it is proposed that a cellular RNA dependent RNA polymerase ("RdRp") binds to the transcript and produces small fragments of antisense RNA which then bind to other transcripts to form duplexes which are then degraded by nucleases that specifically recognize RNA-RNA duplexes. This degradation mechanism is sequence specific, which accounts for the specificity of RNA-mediated resistance.

Work on PVX by Baulcombe and colleagues (English, J. J., et al., "Suppression of Virus Accumulation in Transgenic Plants Exhibiting Silencing of Nuclear Genes," *Plant Cell,* 8: 179–88 (1996); Mueller, E., et al., "Homology-Dependent Resistance: Transgenic Virus Resistance in Plants Related to Homology-Dependent Gene Silencing," *Plant Journal,* 7:1001–13 (1995)) confirmed and extended the results by Dougherty and colleagues. An aberrant RNA model which is a modification of the RNA threshold model proposed by Dougherty and colleagues was proposed. The features of the model are similar to Dougherty's except that it states that the RNA level is not the sole trigger to activate the cellular degradation mechanism, but instead aberrant RNA that are produced during the transcription of the transgene plays an important part in activating the cytoplasmic cellular mechanism that degrades specific RNA. The production of aberrant RNA may be enhanced by positional affects of the transgene on the chromosome and by methylation of the transgene DNA. The precise nature of the aberrant RNA is not defined, but it may contain a characteristic that makes it a preferred template for the production of antisense RNA by the host encoded RdRp (Baulcombe, D. C., "Mechanisms of Pathogen-Derived Resistance to Viruses in Transgenic Plants," *Plant Cell,* 8:1833–44 (1996); English, J. J., et al., "Suppression of Virus Accumulation in Transgenic Plants Exhibiting Silencing of Nuclear Genes," *Plant Cell,* 8: 179–88 (1996)). Thus, the model also proposes that RdRp and antisense molecules are involved in the degradation mechanism. Baulcombe and colleagues confirmed that plants which show low steady state transgene levels have multiple copies of transgenes and that the low steady state RNA and the accompanying resistant state is due to post-transcriptional gene silencing. The term homology-dependent resistance was proposed to describe the resistance in plants that show homology-dependent gene silencing (Mueller, E., et al., "Homology-Dependent Resistance: Transgenic Virus Resistance in Plants Related to Homology-Dependent Gene Silencing," *Plant Journal,* 7:1001–13 (1995)).

Experiments with TSWV tospovirus (Pang, S. Z., et al., "Post-Transcriptional Transgene Silencing and Consequent Tospovirus Resistance in Transgenic Lettuce are Affected by Transgene Dosage and Plant Development," *Plant Journal,* 9:899–09 (1996); Prins, M., et al., "Engineered RNA Mediated Resistance to Tomato Spotted Wilt Virus is Sequence Specific," *Mol. Plant Microbe Interact.,* 9:416–18 (1996)) and cowpea mosaic comovirus (Sijen, T., et al., "RNA-Mediated Virus Resistance: Role of Repeated Transgene and Delineation of Targeted Regions," *Plant Cell,* 8:2227–94 (1996)) also showed that resistance in transgenic plants is a consequence of post-transcriptional gene silencing. Pang, S. Z., et al., "Post-Transcriptional Transgene Silencing and Consequent Tospovirus Resistance in Transgenic Lettuce are Affected by Transgene Dosage and Plant Development," *Plant Journal,* 9:899–09 (1996) showed that post-transcriptional gene silencing in transgenic lettuce expressing the N gene of TSWV was influenced by gene dosage and by the developmental stage of the plant. The effect of developmental stage on post-transcriptional gene silencing of transgenes and their effect on resistance had not been previously shown for transgenic plants expressing viral genes, but had been shown to occur in plants expressing other transgenes (de Carvalho, F., et al., "Suppression of beta-1,3-glucanase Transgene Expression in Homozygous Plants," *EMBO J.,* 11:2595–02 (1992)). Post-transcriptional gene silencing could also account for the correlation of low steady state level of N gene RNA in transgenic tobacco showing very high but specific resistance (Pang, S. Z., et al., "Different Mechanisms Protect Transgenic Tobacco Against Tomato Spotted Wilt and Impatiens Necrotic Spot Tospoviruses," *Bio/Technology,* 11:819–24 (1993)). Prins, M., et al., "Engineered RNA-Mediated Resistance to Tomato Spotted Wilt Virus is Sequence Specific," *Molecular Plant Microbe Interactions,* 9:416–18 (1996) also reported that post-transcriptional gene silencing occurred with transgenic tobacco expressing the N gene and nonstructural gene of the mRNA. Interestingly, it was found that tobacco with other parts of the TSWV genome were not resistant. They suggested, as one explanation, that those gene fragments which did not confer resistance may not fit the criteria for inducing post-transcriptional gene silencing. Sijen, T., et al., "RNA-Mediated Virus Resistance: Role of Repeated Transgene and Delineation of Targeted Regions," *Plant Cell,* 8:2227–94 (1996) showed that resistance of transgenic plants expressing the movement protein, replicase, or coat protein were due to post-transcriptional gene silencing. This data also suggested that the 3' region of the movement protein transgene mRNA is the initial target of the silencing mechanism.

The present invention is directed to producing improved disease resistant plants.

SUMMARY OF THE INVENTION

The present invention is directed to a DNA construct formed from a fusion gene which includes a trait DNA molecule and a silencer DNA molecule. The trait DNA molecule has a length that is insufficient to impart a desired trait to plants transformed with the trait DNA molecule. The silencer DNA molecule is operatively coupled to the trait DNA molecule with the trait and silencer DNA molecules collectively having sufficient length to impart the trait to plants transformed with the DNA construct. Expression systems, host cells, plants, and plant seeds containing the DNA construct are disclosed.

In an alternative embodiment of the present invention, the DNA construct can be a fusion gene comprising a plurality of trait DNA molecules at least some of which having a length that is insufficient to impart that trait to plants transformed with that trait DNA molecule. However, the plurality of trait DNA molecules collectively have a length sufficient to impart their traits to plants transformed with the DNA construct and to effect post-transcriptional silencing of the fusion gene. Expression systems, host cells, plants, and plant seeds containing this embodiment of the DNA construct are disclosed.

The present invention is particular directed to preparing plants which are resistant to multiple viruses. It is well known that particular plant types are often susceptible to more than one virus. Although PDR is an excellent approach to controlling the damaging effects of plant viruses, incorporating multiple virus resistance in a given plant can be challenging. For example, identifying and producing full length viral genes to transform plants can be expensive and time consuming. Further, such genes may be so large that they need to be incorporated in different expression systems which must be separately incorporated in plants.

Rather than attempting to incorporate full length viral genes in a plant, the present invention uses short fragments of such genes to impart resistance to the plant against a plurality of viral pathogens. These short fragments, which each by themselves have insufficient length to impart such resistance, are more easily and cost effectively produced than full length genes. There is no need to include in the plant separate promoters for each of the fragments; only a single promoter is required. Moreover, such viral gene fragments can preferably be incorporated in a single expression system to produce transgenic plants with a single transformation event.

The impact of this simple strategy for multiple virus resistant transgenic plants could have far reaching effects in agriculture. An example is the case of papaya ringspot virus ("PRV"). Transgenic papaya with the coat protein gene of the PRV strain from Hawaii have been developed and found to be highly resistant under greenhouse and long term field conditions. However, that papaya is largely susceptible to strains from other parts of the world, including Jamaica, Thailand, and Brazil. Apparently, PRV resistance in papaya is highly specific and a number of transgenic papaya lines will need to be developed with different coat protein genes of the target countries to control the virus worldwide. With the present invention, a transgenic papaya could be developed with resistance to all PRV strains using viral gene fragments that total less than 1,000 base pairs plus a silencer DNA of about 400 bp; by comparison, the PRV coat protein gene alone is about 1,000 bp.

Another use of the present invention involves imparting resistance against a plurality of different viruses. For example, in potato, the present invention can be employed to impart resistance against potato leaf roll virus, potato virus Y, and potato virus X. To effect such resistance, in accordance with the present invention, a DNA construct, driven by a single promoter, and containing a portion of the potato leafroll virus replicase encoding gene, a portion of the potato virus Y coat protein encoding gene, and a portion of the gene encoding the movement protein of potato virus X can be produced and transformed into potato. As a result, transgenic potato with resistance to potato leafroll virus, potato virus Y, and potato virus X can be produced by a single transformation event. This constitutes a significant advance beyond incorporating full length versions of each of the genes with separate promoters together in a single expression vector or in separate vectors.

Another use of the present invention involves imparting resistance to cucurbits against a number of viruses. For example, in squash, the present invention can be utilized to impart multiple resistance to zuccinni yellow mosaic virus, papaya ringspot virus, watermelon mosaic virus II, and squash mosaic virus. For example, a construct containing a portion of the coat protein encoding gene or a portion of the replicase encoding gene from each of these viruses, driven by a single promoter, can be produced and transformed into squash. The resulting transgenic squash is resistant to all of these viruses.

In addition to conferring on plants resistance to multiple viral diseases, the present invention can be utilized to impart other traits to plants. It is often desirable to incorporate a number of traits to a transgenic plant besides disease resistance. For example, color, enzyme production, etc. may be desirable traits to confer on a plant. However, transforming plants with a plurality of such traits encounter the same difficulties discussed above with respect to disease resistance. The present invention may be likewise useful in alleviating these problems with respect to traits other than disease resistance.

One problem with transforming plants to contain multiple traits is the possibility that not all of them will be successfully imparted. For example, where there are 4 new traits to be imparted to a transgenic plant, there is a 10% likelihood that each expression event will occur, making the probability of imparting all traits in a plant produced in accordance with the present invention much higher than in a plant transformed with full length trait genes driven by separate promoters. More particularly, the probability of expressing all 4 traits in the latter is 0.0001 (i.e., 0.1×0.1×0.1×0.1), while the probability in the present invention is 0.1.

BRIEF DESCRIPTION OF THE DRAWINGS

FIG. 3A is a Northern blot analysis of 8-2 and 8-127 $R_1$ plants. Total RNAs were isolated from transgenic plants (15 μg per lane) and analyzed by Northern blot. Lanes 1 through 6, the silenced 8-2 $R_1$ plants; lanes 7–12, the not silenced 8-127 $R_1$ plants; lane 13, a nontransgenic control. FIG. 3B is a nuclear run-off transcription analysis of $R_1$ plants. Labeled nuclear RNAs were hybridized to restriction enzyme-digested N gene, nptII and actin fragments separated on agarose gel and blotted onto membrane. The nuclei used in the assays were isolated from an 8-2 $R_1$ plant and an 8-127 $R_1$ plant.

DETAILED DESCRIPTION OF THE INVENTION

Figure 1:
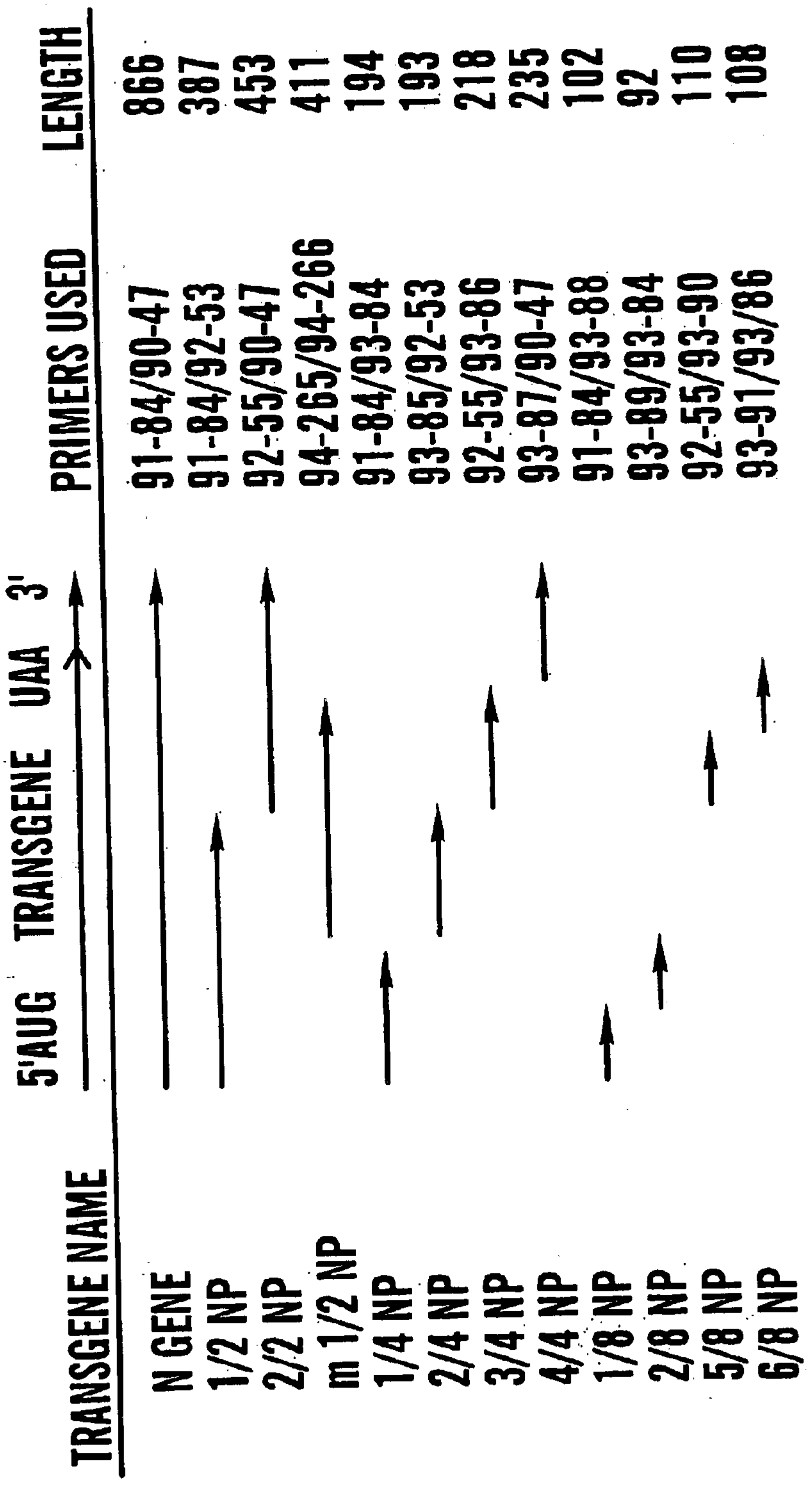
FIG. 1 is a map of the transgenes on the N gene of TSWV-BL.

The present invention is directed to a DNA construct formed from a fusion gene which includes a trait DNA molecule and a silencer DNA molecule. The trait DNA molecule has a length that is insufficient to impart a desired trait to plants transformed with the trait DNA molecule. The silencer DNA molecule is operatively coupled to the trait DNA molecule with the trait and silencer DNA molecules collectively having sufficient length to impart the trait to plants transformed with the DNA construct.

In an alternative embodiment of the present invention, the DNA construct can be a fusion gene comprising plurality of trait DNA molecules at least some of which having a length that is insufficient to impart that trait to plants transformed with that trait DNA molecule. However, the plurality of trait DNA molecules collectively have a length sufficient to impart the traits to plants transformed with the DNA construct and to effect post-transcriptional silencing of the fusion gene.

A particularly preferred aspect of the present invention is where the DNA construct includes a plurality of trait DNA molecules each having a length insufficient to impart the trait to plants transformed with the trait DNA molecule alone. It is also possible for some of the trait DNA molecules to have a length sufficient to impart their respective trait; however, not all such DNA molecules will have such a length.

One aspect of the present invention relates to the use of trait DNA molecules which are heterologous to the plant— e.g., DNA molecules that confer disease resistance to plants transformed with the DNA construct. The present invention is useful in plants for imparting resistance to a wide variety of pathogens including viruses, bacteria, fungi, viroids, phytoplasmas, nematodes, and insects. The present invention may also be used in mammals to impart genetic traits. Resistance, inter alia, to the following viruses can be achieved by the method of the present invention: tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, or combinations thereof. Resistance, inter alia, to the following bacteria can also be imparted to plants in accordance with present invention: *Pseudomonas solancearum, Pseudomonas syringae* pv. *tabaci, Xanthamonas campestris* pv. *pelargonii*, and *Agrobacterium tumefaciens*. Plants can be made resistant, inter alia, to the following fungi by use of the method of the present invention: *Fusarium oxysporum* and *Phytophthora infestans*. Suitable DNA molecules include a DNA molecule encoding a coat protein, a replicase, a DNA molecule not encoding protein, a DNA molecule encoding a viral gene product, or combinations thereof.

The DNA molecule conferring disease resistance can be positioned within the DNA construct in sense orientation. Alternatively, it can have an antisense orientation. Antisense RNA technology involves the production of an RNA molecule that is complementary to the messenger RNA molecule of a target gene; the antisense RNA can potentially block all expression of the targeted gene. In the anti-virus context, plants are made to express an antisense RNA molecule corresponding to a viral RNA (that is, the antisense RNA is an RNA molecule which is complementary to a plus sense RNA species encoded by an infecting virus). Such plants may show a slightly decreased susceptibility to infection by that virus. Such a complementary RNA molecule is termed antisense RNA.

The present invention is also used to confer traits other than disease resistance on plants. For example, DNA molecules which impart a plant genetic trait can be used as the DNA trait molecule of the present invention. In this aspect of the present invention, suitable trait DNA molecules encode for desired color, enzyme production, or combinations thereof.

The silencer DNA molecule of the present invention can be selected from virtually any nucleic acid which effects gene silencing. This involves the cellular mechanism to degrade mRNA homologous to the transgene mRNA. The silencer DNA molecule can be heterologous to the plant, need not interact with the trait DNA molecule in the plant, and can be positioned 3' to the trait DNA molecule. For example, the silencer DNA molecule can be a viral cDNA molecule, a jellyfish green fluorescence protein encoding DNA molecule, a plant DNA molecule, or combinations thereof.

While not wishing to be bound by theory, by use of the construct of the present invention, it is believed that post-transcriptional gene silencing is achieved. More particularly, the silencer DNA molecule is believed to boost the level of heterologous RNA within the cell above a threshold level. This activates the degradation mechanism by which viral resistance is achieved.

It is possible for the DNA construct of the present invention to be configured so that the trait and silencer DNA molecules encode RNA molecules which are translatable. As result, that RNA molecule will be translated at the ribosomes to produce the protein encoded by the DNA construct. Production of proteins in this manner can be increased by joining the cloned gene encoding the DNA construct of interest with synthetic double-stranded oligonucleotides which represent a viral regulatory sequence (i.e., a 5' untranslated sequence). See U.S. Pat. No. 4,820,639 to Gehrke and U.S. Pat. No. 5,849,527 to Wilson which are hereby incorporated by reference.

Alternatively, the DNA construct of the present invention can be configured so that the trait and silencer DNA molecules encode mRNA which is not translatable. This is achieved by introducing into the DNA molecule one or more premature stop codons, adding one or more bases (except multiples of 3 bases) to displace the reading frame, removing the translation initiation codon, etc. See U.S. Pat. No. 5,583,021 to Dougherty et al., which is hereby incorporated by reference.

The subject DNA construct can be incorporated in cells using conventional recombinant DNA technology. Generally, this involves inserting the DNA construct into an expression system to which the DNA construct is heterologous (i.e. not normally present). The heterologous DNA construct may be inserted into the expression system or vector in proper sense orientation and correct reading frame. The vector contains the necessary elements for the transcription of the inserted sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to carry out the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and, perhaps, translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription in procaryotic cells. These transcription initiation signals may vary in "strength" as measured by the quantity of gene specific messenger RNA and protein synthesized, respectively. The DNA expression vector, which contains a promotor, may also contain any combination of various "strong" transcription initiation signals.

Once the DNA construct has been cloned into an expression system, it is ready to be incorporated into a host cell. Such incorporation can be carried out by the various forms of transformation noted above, depending upon the vector/host cell system. Suitable host cells include, but are not limited to, bacteria, virus, plant, and the like cells.

The present invention can also utilize a termination sequence operatively coupled to the fusion gene to end transcription. Suitable transcription termination sequences include the termination region of a 3' non-translated region. This will cause the termination of transcription and the addition of polyadenylated ribonucleotides to the 3' end of the transcribed mRNA sequence. The termination region or 3' non-translated region will be additionally one of convenience. The termination region may be native with the promoter region or may be derived from another source, and preferably includes a terminator and a sequence coding for polyadenylation. Suitable 3' non-translated regions include but are not limited to: (1) the 3' transcribed, non-translated regions containing the polyadenylated signal of *Agrobacterium* tumor-inducing (Ti) plasmid genes, such as the nopaline synthase (NOS) gene or the 35S promoter terminator gene, and (2) plant genes like the soybean 7S storage protein genes and the pea small subunit of the ribulose 1,5-bisphosphate carboxylase-oxygenase (ssRUBISCO) E9 gene.

In producing transgenic plants, the DNA construct in a vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with the DNA construct is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, a vector containing the DNA construct can be introduced into the cell by coating the particles with the vector containing that heterologous DNA construct. Alternatively, the target cell can be surrounded by the vector so that the vector is carried into the cell by the wake of the particle. Biologically active particles (e.g., dried bacterial cells containing the vector and heterologous DNA construct) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859–63 (1982), which is hereby incorporated by reference.

The DNA molecule may also be introduced into the plant cells by electroporation. Fromm et al., *Proc. Natl. Acad. Sci. USA,* 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the $Ri_1$ plasmid of *A. rhizogenes*. The Ti or $Ri_1$ plasmid is transmitted to plant cells on infection by *Agrobacterium* and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

The present invention can be utilized in conjunction with a wide variety of plants or their seeds. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, and sugarcane. Examples of suitable ornamental plants are: *Arabidopsis thaliana, Saintpaulia*, petunia, pelargonium, poinsettia, chrysanthemum, carnation, and zinnia.

EXAMPLES

Example 1

Cloning and Transformation

The N gene (Pang, S.-Z., et al., "Resistance to Heterologous Isolates of Tomato Spotted Wilt Virus in Transgenic Plants Expressing its Nucleocapsid Protein Gene," *Phytopathology,* 82: 1223–29 (1992), which is hereby incorporated by reference) of the lettuce isolate of tomato spotted wilt virus (TSWV-BL) was used as the template for construction of the N gene fragments of various lengths using the primers listed in Table 1.

TABLE 1

Primers used in cloning

| Name | Positions[1] | Sequence |
|---|---|---|
| | | For the N gene fragments |
| 91-84 | 2776-2744 | 5'-AGCTAATCTAGAACCATGGATGACTCACTAAGGAAAGCATTGTTGC (SEQ. ID. NO. 1) |
| 93-89 | 2669-2650 | 5'-TACAGTTCTAGAACCATGGTCTGGAAAACCTTGACCAG (SEQ. ID. NO. 2) |
| 93-85 | 2576-2556 | 5'-TACAGTTCTAGAACCATGGTAAAGCGATTTTACTTTTGGTA (SEQ. ID. NO. 3) |
| 92-55 | 2373-2354 | 5'-AGATTCTCTAGACCATGGTGACTTGATGAGCAAAGTCTGTGAGGCTTGC (SEQ. ID. NO. 4) |
| 93-91 | 2266-2248 | 5'-TACAGTTCTAGAACCATGGAAAATACAAGGATCTCGGG (SEQ. ID. NO. 5) |
| 93-87 | 2153-2133 | 5'-TACAGTTCTAGAACCATGGTAGAAGGGGAAAGAGTATGCTG (SEQ. ID. NO. 6) |
| 90-47 | 1918-1937 | 5'-AGCATTGGATCCATGGTTAACACACTAAGCAAGCAC (SEQ. ID. NO. 7) |

TABLE 1-continued

Primers used in cloning

| Name | Positions[1] | Sequence |
|---|---|---|
| 93-86 | 2158-2177 | 5'-TCTTGAGGATCCATGGCTGATCTTC ATTCATTTCAA (SEQ. ID. NO. 8) |
| 93-90 | 2269-2288 | 5'-TCTTGAGGATCCATGGATCCTGATA TATAGCCAAGA (SEQ. ID. NO. 9) |
| 92-53 | 2383-2402 | 5'-TACAGTGGATCCATGGTTAAGGTAA TCCATAGGCTTGAC (SEQ. ID. NO. 10) |
| 93-84 | 2577-2597 | 5'-TCTTGAGGATCCATGGCTTAATAAC CTTCATTATGC (SEQ. ID. NO. 11) |
| 93-88 | 2671-2690 | 5'-TCTTGAGGATCCATGGAAAAGTCTT GAAGTTGAATG (SEQ. ID. NO. 12) |
| 94-265 | 2556-2530 | 5'-AGCTAATCTAGAACCATGGATGAAA AATTACCATAAAGAAAACTTCAGAC (SEQ. ID. NO. 13) |
| 94-266 | 2182-2206 | 5'-AGCATTGGATCCATGGTTAGTTACC TAGTTTTCTTTTCAGCACAGTGCAAACT (SEQ. ID. NO. 14) |
| 5' TuMV | — | 5'-TTGACTCCATGGCAGGTGAAACGCT TGACG (SEQ. ID. NO. 15) |
| 3' TuMV | — | 5'-GTCGTACCATGGCGAGAATACTAAC GAGTAAAC (SEQ. ID. NO. 16) |
| For the GFP gene | | |
| 5' gfp | NA | 5'-TGAACATCTAGAACCATGGGTAAAG GAGAAGAACTTTTCACTGG (SEQ. ID. NO. 17) |
| 3' gfp | NA | 5'-TGAACAGGATCCATGGTCTACGAAT GCTATTATTTGTATAGTTC (SEQ. ID. NO. 18) |

[1]The nucleotide position number of each primer for the N gene fragments was as published by Pang et al., "Resistance to Heterologous Isolates of Tomato Spotted Wilt Virus in Transgenic Plants Expressing its Nucleocapsid Protein Gene," Phytopathology, 82: 1223–29 (1992), which is hereby incorporated by reference.

The forward primers for the N gene fragments were designed to contain an out-of-frame ATG and/or stop codons to ensure the production of untranslatable N gene transcripts. The PCR-amplified N gene fragments (Table 2) were cloned in the sense orientation into the NcoI site of plant expression vector pBI525 (Pang, S.-Z., et al., "Resistance to Heterologous Isolates of Tomato Spotted Wilt Virus in Transgenic Plants Expressing its Nucleocapsid Protein Gene," *Phytopathology,* 82:1223–29 (1992), which is hereby incorporated by reference).

TABLE 2

Reactions of $R_1$ plants expressing the N gene fragments to inoculations with the TSWV-BL isolate.

| Gene | Size (bp) | # tested lines | # tested plants | # resistant lines | Reactions of test plants[a] HS | HT | HR |
|---|---|---|---|---|---|---|---|
| control | | | 239 | | 239 | | |
| 2/2N | 453 | 7 | 118 | 5 | 63 | 26 | 29 |
| m1/2N | 411 | 6 | 108 | 6 | 36 | 17 | 55 |
| 1/2N | 387 | 5 | 99 | 2 | 75 | 4 | 20 |
| 4/4N | 235 | 7 | 89 | 0 | 89 | | |
| 3/4N | 218 | 12 | 145 | 0 | 145 | | |
| 1/4N | 194 | 12 | 134 | 0 | 134 | | |
| 2/4N | 193 | 5 | 64 | 0 | 64 | | |
| 5/8N | 110 | 7 | 85 | 0 | 85 | | |
| 6/8N | 108 | 13 | 162 | 0 | 162 | | |
| 1/8N | 102 | 14 | 170 | 0 | 170 | | |
| 2/8N | 92 | 8 | 63 | 0 | 63 | | |

[a]30-fold diluted leaf extracts of the *N. benthamiana* plants infected with TSWV-BL were applied to three upper leaves of the plants at the 5–7 leaf stage. Data were taken every other dayfor at least 45 days. The reactions could be grouped into three phenotypes: 1) highly susceptible ("HS"), typical systemic symptoms were observed at 5–10 days after inoculation;2) highly tolerant ("HT"), systemic symptoms were significantly delayed (more than 10 days post inoculation); 3) highly resistant ("HR"), the plants remained symptom free throughout their life cycles. See FIG. 1 for the definition of the N gene of TSWV-BL.

For construction of various N gene fragment fusions with green fluorescent protein ("GFP"), the translatable GFP open reading frame ("ORF") was amplified with GFP primers (Table 1) from the plasmid PGFP (Clontech, Palo Alto, Calif.) and cloned as transcriptional fusions into the 5' NcoI site of the N gene fragments 2/2N, 3/4N, and 5/8N in pBI525. The resulting GFP/N fusions contained translatable GFP ORF followed by untranslatable N gene fragments of different lengths as the 3' untranslated regions of the GFP gene.

The resulting above plant expression vectors were digested with HindIII and EcoRI (partial digestion where necessary), and the HindIII-EcoRI fragments containing the corresponding gene cassettes were isolated and introduced into the same sites of pBIN19. The resulting binary vectors were transferred to *Agrobacterium tumefaciens* LBA4404 and the *A. tumefaciens* containing the vectors were used to inoculate leaf discs of *Nicotiana benthamiana* plants, essentially as described by Horsch et al. (Horsch, R. B., et al., "A Simple and General Method for Transferring Genes into Plants," *Science,* 227:1229–31 (1985), which is hereby incorporated by reference).

Example 2

ELISA, Northern Blot Analyses of Transgenic Plants

Double antibody sandwich enzyme-linked immunosorbent assay ("DAS-ELISA") was used to detect the nptII enzyme in transgenic plants using an nptII ELISA kit (5

Prime to 3 Prime, Inc). Northern blot was performed as described previously (Pang, S. Z., et al., "Different Mechanisms Protect Transgenic Tobacco Against Tomato Spotted Wilt and Impatiens Necrotic Spot Tospoviruses," *Bio/Technology,* 11: 819–24 (1993), which is hereby incorporated by reference).

Example 3

Inoculation of Transgenic Plants

Inoculations were done as described previously (Pang, S.-Z., et al., "Resistance to Heterologous Isolates of Tomato Spotted Wilt Virus in Transgenic Plants Expressing its Nucleocapsid Protein Gene," *Phytopathology,* 82: 1223–29 (1992), which is hereby incorporated by reference). Systemic symptoms were recorded every other day for at least two months.

Example 4

Isolation of Nuclei and Nuclear Run-Off Transcription Assays

Isolation of nuclei and nuclear run-off transcription assays were previously described (Pang, S. Z., et al., "Post-Transcriptional Transgene Silencing and Consequent Tospovirus Resistance in Transgenic Lettuce are Affected by Transgene Dosage and Plant Development," *Plant Journal,* 9: 899–09 (1996), which is hereby incorporated by reference).

Example 5

Small N Gene Fragments (92–235 bp) Do Not Induce RNA-Mediated Tospovirus Resistance The untranslatable N gene fragments of 92 bp to 453 bp in length (Table 2) were PCR amplified using appropriate sets of the 5' and 3' primers (Table 1). The 5' primers were designed to contain an out-of-frame ATG followed by stop codons to prevent the translation of truncated N protein. The N gene fragments, representing various regions of the entire N gene (FIG. 1; Table 2), were cloned in the sense orientation into the plant expression vector pBI525. This vector utilized the double enhanced CaMV 35S promoter, the 5' untranslated region from alfalfa mosaic virus ("AIMV"), and the 3' untranslated region of nopaline synthase gene. The resulting expression cassettes were used to obtain transgenic *N. benthamiana* plants via *Agrobacterium* mediated transformation.

Figure 2:
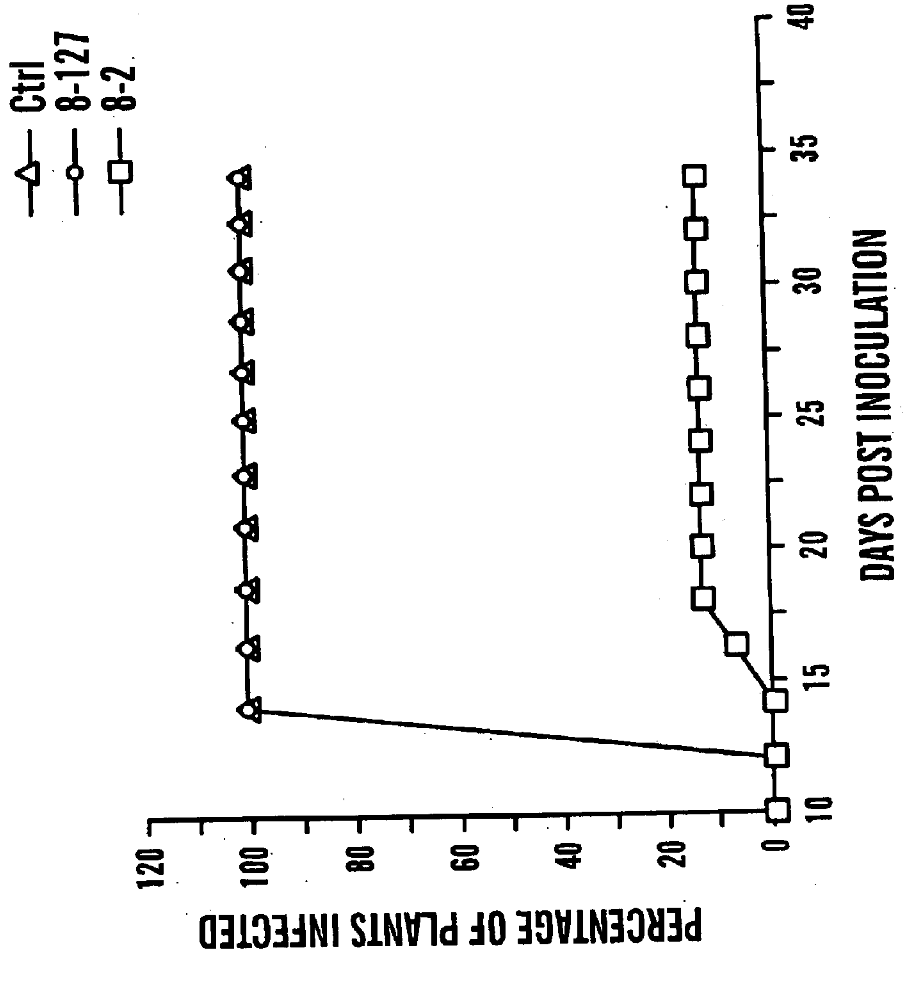
FIG. 2 shows the protection of transgenic plants against infection by TSWV-BL. $R_1$ plants of selected lines (a ½N high expressor 8-127 and a ½N low expressor 8-2, as determined by Northern blot analysis) were assayed by DAS-ELISAs for nptII using an nptII ELISA kit (5 Prime to 3 Prime, Inc.). The ELISA negative nontransgenic segregates (nptII ELISA readings of 0.00–0.02 $OD_{405\ nm}$) were used as controls. The same plants were then challenged with TSWV-BL. Plants were examined every other day for the appearance of systemic symptoms, and any plant displaying symptoms on noninoculated leaves was recorded as systemic infection.
Figure 3A:
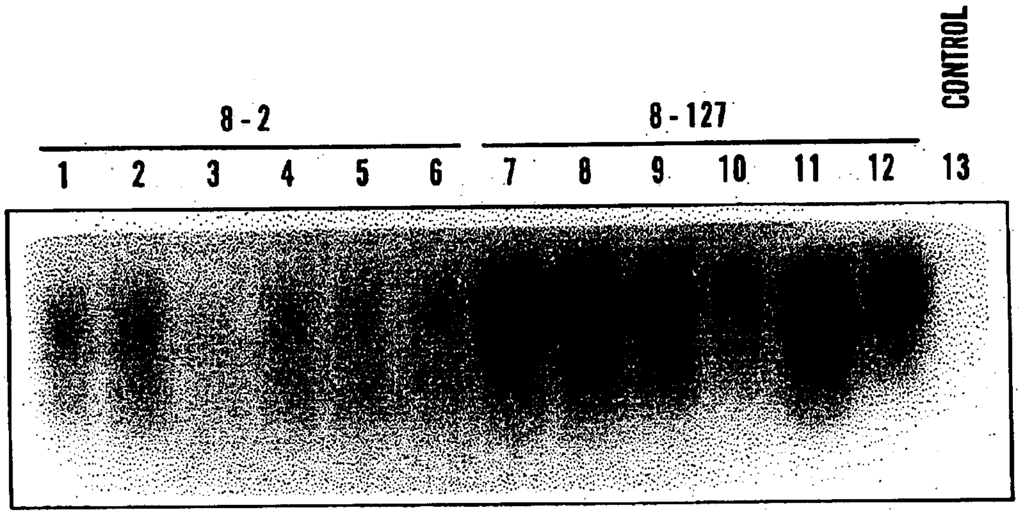
FIGS. 3A–B show transgene silencing in the ½N low expressor 8-2.
Figure 3B:
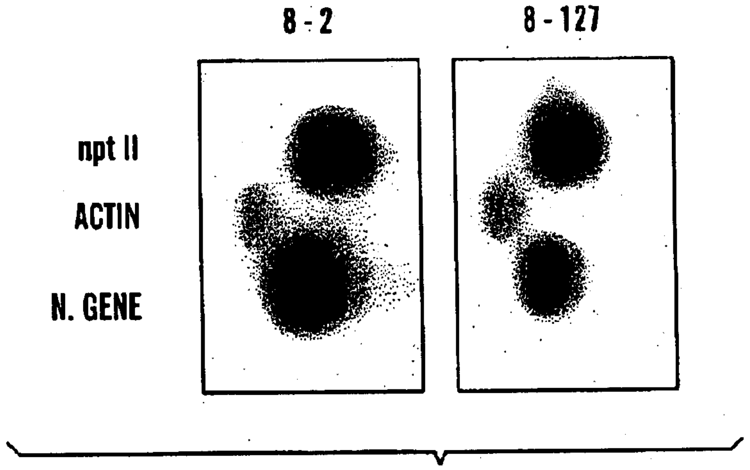

Transgenic $R_1$ seedings were initially screened with the nptII ELISA to identify nontransgenic segregates from the $R_1$ transgenic populations. In order to exclude the possibility of escapes and avoid human bias during inoculation, nontransgenic segregates from each of the lines were inoculated as internal controls along with transgenic $R_1$ plants. Additionally, nontransformed *N. benthamiana* plants were also included in each inoculation experiments. Reactions of the inoculated $R_1$ plants to TSWV-BL are summarized in FIG. 2 and Table 2. Unlike negative control plants which were completely susceptible to the virus, expression of large N gene fragments (387–453 bp, one half N gene) conferred high levels of resistance to TSWV-BL in 20–51% of $R_1$ plants and tolerance to tospovirus infection in 4–22% of $R_1$ plants. The $R_1$ plants were also shown to be resistant to a closely related TSWV-10W isolate but not to the distantly related Impatiens necrotic spot virus ("INSV") (Law, M. D., et al., "The M RNA of Impatiens Necrotic Spot Tospovirus (Bunyaviridae) Has an Ambisense Genomic Organization," *Virology,* 188:732–41 (1992), which is hereby incorporated by reference) or Groundnut ringspot virus ("GRSV") (Pang, S. Z., et al., "The Biological Properties of a Distinct Tospovirus and Sequence Analysis of its mRNA," *Phytopathology,* 83:728–33 (1993), which is hereby incorporated by reference) isolates. Northern analysis on selected lines showed correlation of the resistant phenotype with low levels of the N gene fragment transcript accumulation (FIG. 3A). To confirm that the reduced steady-state mRNA levels of the N gene fragments were due to post-transcriptional down-regulation of the transgene, nuclear run-off transcription analysis was performed. Using the endogenous actin as a control, the N gene fragments were found to be transcribed in the silenced progenies at higher rates than in the nonsilenced high-expressing progenies (FIG. 3B). These results collectively suggested that the resistance observed was the result of post-transcriptional transgene silencing, which affected the steady-state mRNA accumulation but not transcription rate.

Figure 4:
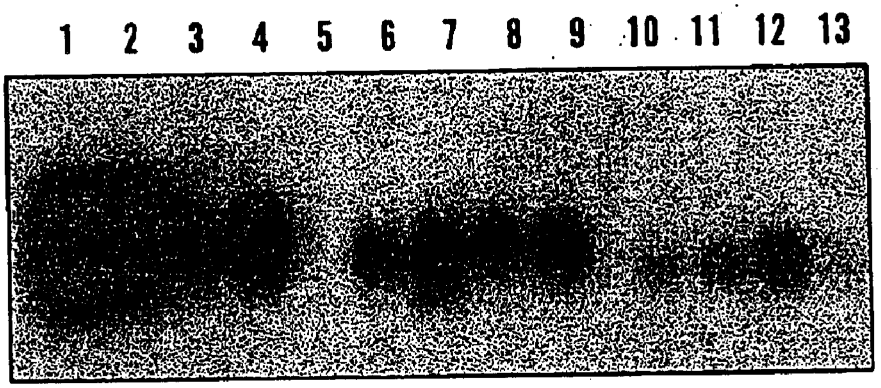
FIG. 4 compares transcript accumulations in plants expressing the N gene fragments of different lengths. Lanes 1 and 2, two not silenced, virus susceptible $R_1$ plants with the full-length N gene; lane 3, a silenced, virus resistant $R_1$ plant with ⅔N gene; lane 4, a not silenced, virus susceptible $R_1$ plant with the ⅔N gene; lanes 5–8; four not silenced, virus susceptible $R_1$ plants with the ¾N gene; lanes 9–12, four not silenced, virus susceptible $R_1$ plants with the ⅝N gene.

$R_1$ plants expressing the small N gene fragments (92–235 bp, one fourth to one eighth NP) were similarly inoculated with TSWV-BL and other tospovirus isolates, and all of them were susceptible to tospovirus infection (Table 2). Northern blot analysis of selected $R_1$ plants showed that the transcript level of the N gene fragments correlated with the length of transgenes. As shown in FIG. 4, the transcripts of large transgenes generally accumulated at much higher levels than those of small transgenes in the nonsilenced $R_1$ plants (FIG. 4). This result suggested that the small N gene fragments were not effectively transcribed in the nuclei, or were transcribed at similar rates but were not properly processed, transported, or stable in the cytoplasms. As a result, there was no induction of transgene silencing in those small transgene plants. In fact, a number of representative lines expressing the small N gene fragments were analyzed by nuclear run-off transcription analysis, and the results showed no evidence that post-transcriptional silencing took place in any of those tested lines.

Example 6

Fusions of the Small N Gene Fragments with GFP Confer RNA-Mediated Tospovirus Resistance It was possible that the inability of the small N gene fragments to confer RNA-mediated resistance was because the transgenes were too small to be expressed and accumulate at high levels (e.g., inefficient transcription, processing, transport or less stability) or because the small N gene fragments fell below the minimal length of homology for trans-inactivation of the incoming virus genome. Various N gene fragments (110, 218, and 453 bp) were fused to the 3' end of the GFP gene, as described supra. Expression of such fusions in plants cells produces transcripts consisting of functional GFP open reading frame immediately followed by the respective N fragments as the 3' untranslated region. $R_0$ plant expressing these fusions were inoculated with the homologous isolate TSWV-BL and inoculation results are summarized in Table 3. As a control, transgenic $R_0$ plants expressing GFP alone displayed typically systemic symptoms at 5–10 days post inoculation. On the other hand, all GFP/N fusions conferred various levels of resistance to TSWV-BL (Table 3), including the small N fragments (110 bp and 218 bp) which provided no protection against TSWV-BL when expressed alone in plants (Table 2).

TABLE 3

Reactions of $R_0$ plants expressing GFP/N fusions to inoculations with the TSWV-BL isolate.

| Gene | Size (bp) | # line | Reactions of test plants[a] HS | HT | HR |
|---|---|---|---|---|---|
| GFP | 720 + 0 | 8 | 8 | | |
| GFP + 5/8N | 720 + 110 | 13 | 11 | 1 | 1 |
| GFP + 3/4N | 720 + 218 | 8 | 2 | | 6 |
| GFP + 2/2N | 720 + 453 | 14 | 5 | 1 | 8 |

[a]30-fold diluted leaf extracts of the *N. benthamiana* plants infected with TSWV-BL were applied to three upper leaves of the plants at the 5–7 leaf stage. Data were taken every other day for at least 45 days. The reactions could be grouped into three phenotypes: 1) highly susceptible ("HS"), typical systemic symptoms were observed at 5–10 days after inoculation;2) highly tolerant ("HT") , systemic symptom was significantly delayed (more than 10 day post inoculation); 3) highly resistant ("HR"), the plants remained symptom free throughout their life cycles.

$R_1$ progeny from selected $R_0$ lines were similarly inoculated and they showed similar levels of protection against TSWV-BL (Table 4).

TABLE 4

Reactions of $R_1$ plants expressing GFP/N fusions to inoculations with the TSWV-BL isolate.

| Gene | line # | # plants tested | Reactions of test plants[a] HS | HT | HR |
|---|---|---|---|---|---|
| GFP + 5/8N | 1 | 18 | 10 | 7 | 1 |
| | 3 | 14 | 14 | | |
| GFP + 3/4N | 5 | 17 | | 8 | 9 |
| | 6 | 18 | | 6 | 12 |
| | 7 | 18 | 15 | | 3 |
| | 22 | 20 | | | 20 |
| | 23 | 20 | 16 | 1 | 3 |
| | 24 | 16 | | | 16 |
| GFP + 2/2N | 8 | 15 | 9 | 1 | 5 |
| | 9 | 18 | 18 | | |
| | 10 | 16 | 16 | | |
| | 26 | 22 | 19 | 3 | |
| | 27 | 19 | 19 | | |
| | 28 | 21 | 18 | 1 | 2 |
| | 29 | 21 | | 1 | 20 |

[a]30-fold diluted leaf extracts of the *N. benthamiana* plants infected with TSWV-BL were applied to three upper leaves of the plants at the 5–7 leaf stage. Data were taken every other day for at least 45 days. The reactions could be grouped into three phenotypes: 1) highly susceptible ("HS"), typical systemic symptoms were observed at 5–10 days after inoculation; 2) highly tolerant ("HT"), systemic symptom was significantlydelayed (more than 10 day post inoculation); 3) highly resistant ("HR") , the plants remained symptom free throughout their life cycles.

Figure 5:
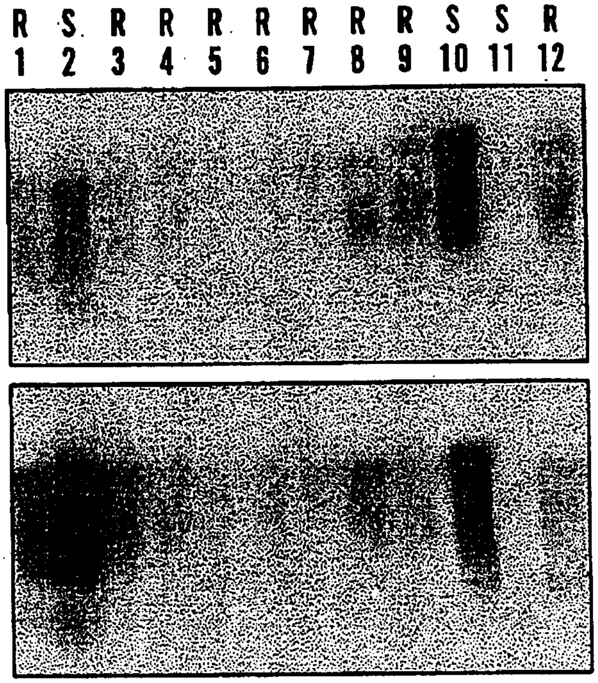
FIG. 5 shows a Northern analysis of $R_1$ plants containing the GFP/N fusions. Leaves were harvested for RNA isolation when the plants were at the 5–6 leaf stage. Ten μg per lane of total RNA were used for Northern blot which was probed with the N gene of TSWV-BL (top row) or GFP gene (bottom row). After removal of leaf samples for RNA analysis, the plants were inoculated with TSWV-BL and assigned as either resistant ("R") or susceptible ("S") depending on the presence or absence of systemic symptoms at 14 days post-inoculation. Lanes 1–2, GFP+⅝N–1 $R_1$ plant; lanes 3–6, GFP+¾N–5 $R_1$ plants; lane 7, GFP+¾N–6 $R_1$ plants; lane 8, GFP+¾N–23 $R_1$ plants; lanes 9–10 and 12, GFP+¾N–8 $R_1$ plants; lane 11, a nontransformed plant.

The $R_1$ plants were also shown to be resistant to a closely related TSWV-10W isolate but not to the distantly related INSV or GRSV isolate. These results suggest that the GFP gene triggered gene silencing which degraded GFP and the small targeted N gene fragments, and the homologous sequences of the incoming virus which resulted in the resistant state of the plant. However, the smallest GFP–5/8 N fusion (110 bp of homology) was less effective against TSWV-BL, as reflected by the fewer number of $R_0$ plants protected and the quality of protection (Tables 3 and 4), indicating that the 110 bp of nucleotide sequence may approach the shortest homology required for trans-inactivation and consequent virus resistance. In addition, some of the $R_1$ plants expressing the fusions were analyzed by Northern blot using both N gene and GFP gene as probes (FIG. 5). Northern results showed that the observed resistance again correlated with low accumulation levels of the fusion gene transcripts, suggesting that the same resistance mechanism operates in plants expressing the N gene fragments alone or the GFP/N fusions.

A number of plant lines that express different regions of TSWV N gene alone or fused with a non-viral sequence, GFP, were generated. Transgenes smaller than one quarter (235 bp) of the N gene were ineffective when expressed alone but were effective when fused to the GFP gene for post-transcriptional inactivation of the homologous, incoming tospovirus. This result suggests that the inability of the small N transgenes alone to induce homology-dependent virus resistance was not due to their insufficient lengths of homology to the silenced transgene (in this case the virus genome) but because they are incapable of inducing gene silencing. Thus, this study differentiates the ability to induce transgene silencing from the ability to provide homology-dependent trans-inactivation.

Example 7

Figure 7:
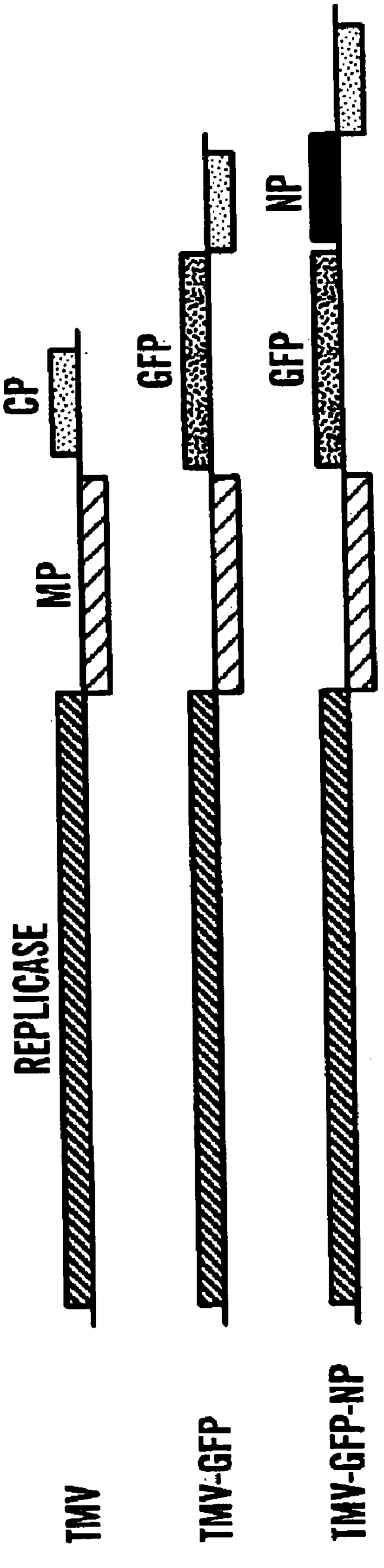
FIG. 7 is a schematic diagram of TMV-GFP and TMV-GFP—NP. TMV-GFP was obtained from Dr. C. A. Holt. The N gene sequence of TSWV was transcriptionally fused with GFP at the NotI site. In vitro transcription was performed as described by Casper et al., "Expression of the Green Fluorescent Protein-Encoding Gene from Tobacco Mosaic Virus-Based Vector," *Gene*, 173:69–73 (1996), which is hereby incorporated by reference.

Fusions of the Small N Gene Fragments with GFP or TuMV-CP Confer RNA-Mediated Multiple Resistance Transgenic plants with various N gene fragments (2/2N, 3/4N, and 5/8N) fused to the 3'-end of the GFP confer Tospovirus resistance in both $R_0$ and $R_1$ progenies (Tables 3 and 4). English et al., "Suppression of Virus Accumulation in Transgenic Plants Exhibiting Silencing of Nuclear Genes," *Plant Cell,* 8:179–88 (1996), which is hereby incorporated by reference, reports that transgenic plants with silenced transgene can inactivate a chimeric virus containing the transgene sequence since the degrading mechanism in the silenced plants can recognize the silenced sequence in the incoming chimeric virus. To determine whether the transgenic plants with GPF/N fusions can be resistant to TSWV as well as a chimeric virus with GFP sequence since both the GFP and N fragment were silenced in the TSWV resistance plants (FIG. 5), R2 transgenic plants with GFP/N fusions were inoculated with TSWV, TMV-GFP, and TMV-GFP—NP (FIG. 7). As shown in Table 5, transgenic plants with GFP/N fusions are resistant to both TSWV and TMV-GFP. This data shows that small N fragments linked with a silencer (here GFP) can confer multiple resistance in transgenic plants.

TABLE 5

Reactions of R2 progeny of transgenic plants expressing GFP–2/2N, GFP–3/4N and GFP–5/8N to TSWV, TMV-GFP, and TMV-GFP-NP

| | TSWV n | R | S | TMV-GFP n | R | S | TMV-GFP-NP n | R | S |
|---|---|---|---|---|---|---|---|---|---|
| GFP – 2/2N | | | | | | | | | |
| 4–11 (8) 373 | 21 | 12 | 9 | NT | | | NT | | |
| GFP – 3/4N | | | | | | | | | |
| 3–10 (5) 193 | 26 | 26 | 0 | 4 | 4 | 0 | 4 | 4 | 0 |
| 3–10 (6) 250 | 35 | 35 | 0 | NT | | | NT | | |
| GFP – 5/8N | | | | | | | | | |
| 2–6 (1) 3 | 38 | 38 | 0 | 4 | 4 | 0 | 4 | 4 | 0 |
| control | 12 | 0 | 12 | 12 | 1 | 11 | 12 | 1 | 11 |

TABLE 5-continued

Reactions of R2 progeny of transgenic plants expressing GFP−2/2N, GFP−3/4N and GFP−5/8N to TSWV, TMV-GFP, and TMV-GFP-NP

| | TSWV | | | TMV-GFP | | | TMV-GFP-NP | | |
|---|---|---|---|---|---|---|---|---|---|
| | n | R | S | n | R | S | n | R | S |

TSWV-BL infected leaf extracts (1/30) (Pang et al., "Nontarget DNA Sequences Reduce the Transgene Length Necessary for RNA-Mediated Tospovirus Resistance in Transgenic Plants," Proc. Natl. Acad. Sci.USA, 94: 8261–8266 (1997), which is hereby incorporated by reference) or infectious transcripts of TMV-GFP produced by in vitro transcription (Casper et al., "Expression of the Green FluorescentProtein-Encoding Gene from Tobacco Mosaic Virus-based Vector," Gene, 173: 69–73 (1996), which is hereby incorporated by reference) were applied to three upper leaves of *N. benthamiana*, at the 5–7 leaf stage. Susceptible (S) plant show typical systemic symptoms 5–10 days after TSWV inoculation or show green fluorescence on inoculated leaves 2–5 DPI and upper leaves 4–6 DPI when infected with TMV-GFP. Resistant (R) plants remained symptomless at 30 DPI.

Figure 6:
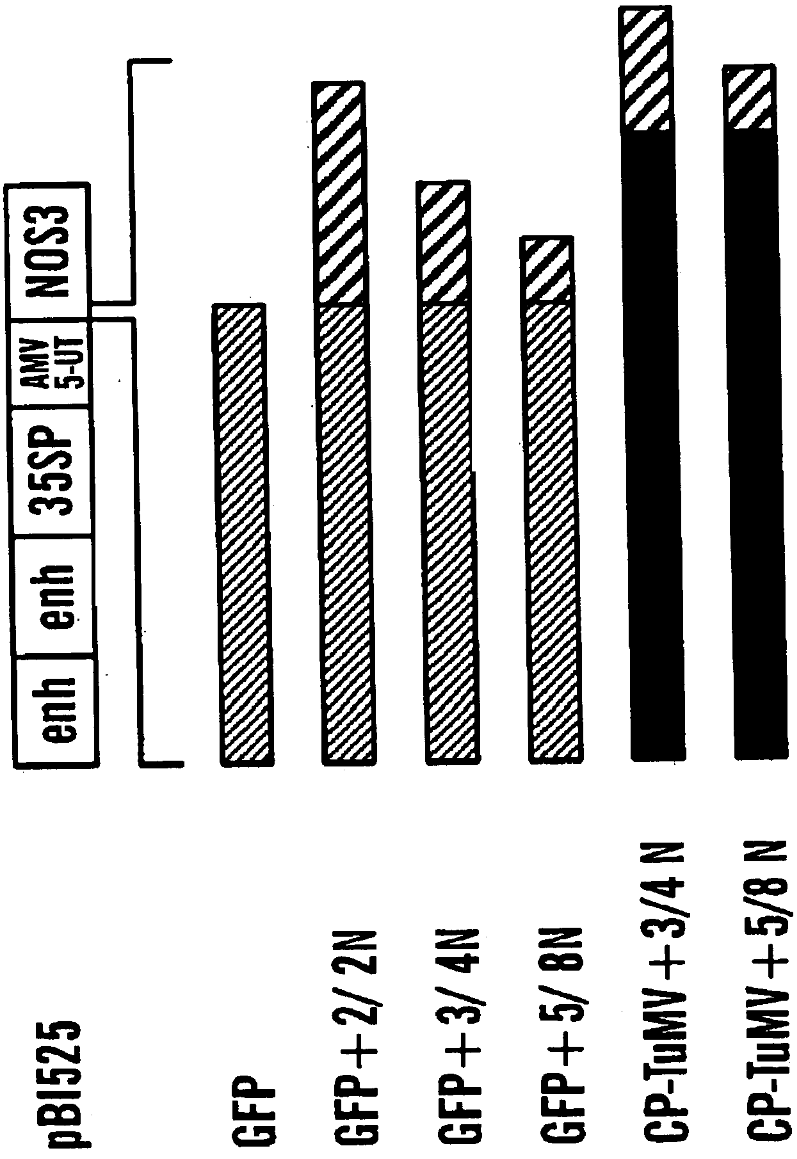
FIG. 6 is a map of the transgenes used in this study. A nontranslatable N gene segment was transcriptionally fused with GFP or CP-TuMV gene. Each transgene was driven by double enhanced CaMV 35S promoter, 5'-untranslated leader of alfalfa mosaic virus, and 3'-untranslated sequence of the nopaline synthase gene. The whole expression cassette was inserted into the plant transformation vector, pBIN19 (Clontech Laboratories, Inc.), and then introduced into *Nicotiana benthamiana* via leaf disc transformation by *Agrobacterium tumafaciens* LBA4404. ⅔ N is the second half, ¾ N is the third quarter, ⅝N is the ⅝th of the N gene of TSWV-BL. Pang et al., "Nontarget DNA Sequences Reduce the Transgene Length Necessary for RNA-Mediated Tospovirus Resistance in Transgenic Plants," *Proc. Natl. Acad. Sci. USA*, 94:8261–66 (1997), which is hereby incorporated by reference.

Other DNA transgenes (besides the GFP DNA) could be used to link the N gene fragments and still induce silencing. If the 'silencing' DNA is of viral origin, it could also serve as a viral transgene for imparting resistance, resulting in multiple resistance. This was tested with the ¼ and ⅛N gene fragments of TSWV which were linked to the turnip mosaic potyvirus (TuMV) coat protein gene and mobilized into *N. benthamiana* (FIG. 6). R1 progeny were inoculated with TuMV or TSWV. Reactions of the inoculated R1 plants to TSWV-BL and TuMV are summarized in Table 6. Unlike negative control plants, which were completely susceptible to the viruses, four lines of transgenic plants with TuMV CP-¾N and one line of TUMV CP-⅝N conferred resistance to TuMV as well as TSWV.

TABLE 6

Reaction segment linked to CP of TuMV to inoculations with TuMV ESC8 and TSWV-BL

| | Reaction to TSWV | | | | Reaction to TuMV | | | |
|---|---|---|---|---|---|---|---|---|
| | # tested | S | D | R | # tested | S | D | R |
| CP − 3/4N | | | | | | | | |
| 55-3 | 10 | 10 | 0 | 0 | 10 | 7 | 3 | 0 |
| 55-4 | 11 | 5 | 4 | 2 | 12 | 7 | 2 | 3 |
| 55-23 | 12 | 12 | 0 | 0 | 12 | 12 | 0 | 0 |
| 55-6 | 8 | 2 | 4 | 2 | 10 | 1 | 2 | 7 |
| 55-10 | 12 | 12 | 0 | 0 | 10 | 3 | 7 | 0 |
| 55-9 | 28 | 18 | 7 | 3 | 29 | 8 | 8 | 13 |
| 55-17 | 16 | 14 | 1 | 1 | 16 | 6 | 2 | 8 |
| 55-21 | 13 | 13 | 0 | 0 | 21 | 5 | 3 | 13 |
| 55-15 | 17 | 17 | 0 | 0 | 11 | 11 | 0 | 0 |
| 55-20 | 14 | 14 | 0 | 0 | 17 | 4 | 0 | 13 |
| 55-14 | 16 | 16 | 0 | 0 | 16 | 16 | 0 | 0 |
| 55-19 | 17 | 17 | 0 | 0 | 18 | 18 | 0 | 0 |
| 55-8 | 16 | 16 | 0 | 0 | 20 | 3 | 9 | 8 |
| 55-13 | 16 | 16 | 0 | 0 | 20 | 15 | 5 | 0 |
| 55-16 | 16 | 16 | 0 | 0 | 19 | 10 | 7 | 2 |
| 55-12 | 20 | 20 | 0 | 0 | 13 | 13 | 0 | 0 |
| 55-2 | 17 | 17 | 0 | 0 | 15 | 15 | 0 | 0 |
| 55-11 | 19 | 19 | 0 | 0 | 23 | 4 | 12 | 7 |
| CP − 5/8N | | | | | | | | |
| 125-7 | 19 | 11 | 8 | 0 | 19 | 18 | 1 | 0 |
| 125-8 | 15 | 15 | 0 | 0 | 16 | 16 | 0 | 0 |
| 125-9 | 18 | 18 | 0 | 0 | 17 | 17 | 0 | 0 |
| 125-10 | 24 | 24 | 0 | 0 | 21 | 21 | 0 | 0 |
| 125-11 | 12 | 12 | 0 | 0 | 14 | 14 | 0 | 0 |
| 125-12 | 20 | 14 | 4 | 2 | 19 | 15 | 2 | 2 |
| 125-13 | 14 | 14 | 0 | 0 | 14 | 14 | 0 | 0 |

TABLE 6-continued

Reaction segment linked to CP of TuMV to inoculations with TuMV ESC8 and TSWV-BL

| | Reaction to TSWV | | | | Reaction to TuMV | | | |
|---|---|---|---|---|---|---|---|---|
| | # tested | S | D | R | # tested | S | D | R |
| 125-14 | 21 | 21 | 0 | 0 | 21 | 21 | 0 | 0 |
| 125-15 | 11 | 11 | 0 | 0 | 12 | 12 | 0 | 0 |
| 125-17 | 17 | 17 | 0 | 0 | 11 | 11 | 0 | 0 |
| 125-18 | 11 | 11 | 0 | 0 | 10 | 10 | 0 | 0 |
| 125-19 | 11 | 11 | 0 | 0 | 9 | 9 | 0 | 0 |
| 125-20 | 16 | 16 | 0 | 0 | 8 | 8 | 0 | 0 |
| 125-21 | 12 | 12 | 0 | 0 | 12 | 12 | 0 | 0 |

30-fold diluted leaf extracts of TuMV-ESC8 or TSWV-BL were applied to three upper leaves of the plants at the 5–7 leaf stages. Data were taken every other day for at least 45 days. The reactions could be grouped into three phenotypes: 1) Susceptible(S), typical systemic symptoms were observed at 5–8 days after inoculation; 2) Delayed (D), systemic symptom was significantly delayed (3–16 days delayed compared to control susceptible plants); and 3) Resistant (R), the plants grew and developed normallythroughout their life cycles even though some of them showed mild mosaic symptoms on the new growing leaves and disappeared when the leaves were fully expanded at the late developmental stages. Those mild mosaic symptoms did not seem to affect any phase of normal plant growth and development.

This data demonstrates the following points: 1) that gene silencing can be induced by the GFP, TSWV, and TuMV transgenes; 2) ½N gene lengths, but not ¼N and ⅛N gene lengths, can confer resistance; 3) the minimum length of viral transgene (TSWV N gene) that can confer resistance is significantly reduced (i.e. down to ⅛N gene) when it is linked to a DNA (i.e. GFP) that triggers post transcriptional gene silencing; and 4) the DNA that triggers silencing of the linked viral gene fragments can itself be a viral gene, as shown with TuMV. These results serve as the basis to develop a simple and effective new strategy for engineering multiple virus resistance by linking several small viral DNA fragments with a silencer DNA (GFP, viral sequence, as well as any interesting gene from plants, animals, or other organisms). This data also raises the possibility of developing a simple and effective new strategy for controlling and regulating gene expression, enzyme or protein production, and any kind of interesting phenotype in transgenic plants.

Inability of the small N gene fragments to induce transgene silencing can be due to their inefficient transcription in nuclei, inefficient processing/transport and/or less stability of their transcripts in the cytoplasms. This conclusion is consistent with the Northern Blot analysis, showing that the transcript of the small transgenes accumulated at much lower levels in the cytoplasms than that of the large transgenes (FIG. 4). The reduced transcript accumulation of the small transgenes may result from steric interference of transcription initiation machinery with the transcription termination machinery. Alternatively, the small N gene transcripts may lose critical RNA sequence elements required for effective mRNA processing, transport and/or stability, resulting in much less mature mRNA accumulation in the cytoplasms (Caponigro, G., et al., "Mechanisms and Control of mRNA Turnover in *Sacharomyces cerevisiae,*" *Microbiological Reviews* 60:233–49 (1996), which is hereby incorporated by reference). The addition of the GFP gene to the small transgenes may simply enhance their ability to transcribe the transgene lengths, or the GFP gene may provide RNA sequence elements required for accumulation of the mature mRNA.

On the other hand, trans-inactivation of the silenced transgene requires much shorter sequence of homology. In this case, when expressed as a fusion with GFP, transgenes as short as 110 bp can trans-inactivate the incoming virus genome. This short homologous sequence presumably interacts with the incoming virus to form a RNA duplex, which serves as a target for cellular degradation. The observation that the smallest fusion transgene GFP–⅝N was inefficient in conferring virus resistance (Tables 3 and 4) indicates that 110 bp (⅛th NP) sequence of homology may be approaching the minimal length of homology required for trans-inactivation of the silenced genes (in this case the virus genome). This result is consistent with the recent observation of Sijen, T., et al., "RNA-Mediated Virus Resistance: Role of Repeated Transgene and Delineation of Targeted Regions," *Plant Cell,* 8:2227–94 (1996), which is hereby incorporated by reference. They showed that a small homologous sequence of only 60 nucleotides was sufficient to tag a recombinant PVX molecule for the gene-silencing-mediated elimination process. They also showed that the frequency and quality of resistance appeared to depend on both the length of the homologous sequence and the inoculum concentration.

Any part of the N gene (first half, middle, or second half) can confer post-transcriptional gene silencing-derived viral resistance (Table 2). This result suggests that the specific RNA secondary structure of the N gene sequence might not be necessary for inducing transgene silencing and viral resistance. Small fragments (110–235 bp) were ineffective when expressed alone but were effective when fused to the GFP gene for post-transcriptional gene silencing and viral resistance. Taken together, the post-transcriptional gene silencing-derived virus resistance is transgene length dependent. It also seems that any part of the N gene larger than 110 bp can confer resistance when it is fused with GFP. These results also indicate that any small part of the viral genome larger than a certain length might confer resistance when fused with a silencer DNA (e.g. GFP).

This study showed that homology-dependent virus resistance can be obtained by fusing small viral sequences to the GFP gene. This observation leads to the view that any viral sequence longer than 110 bp could confer RNA-mediated resistance when fused to stably expressed, normal length nonviral transgene. If it is true, it would significantly facilitate the engineering of viral resistance, because isolation of a specific viral gene such as coat protein gene or replicase gene can be very tedious, especially if the viral genome organization is not well characterized. It should be pointed out that the coat protein gene will continue to be one of the best choices for RNA-mediated resistance, because it is highly expressed and its transcript is presumably very stable in the infected cells.

Transgenic plants which show post-transcription gene silencing-derived resistance establish the highly resistant state and prevent virus replication. A chimeric transgene consisting of a silencer DNA (e.g., GFP) fused with various small nontranslatable fragment viral genome would be preferred for viral resistance. There are several advantages. First, the silencer DNA can increase the induced gene silencing. Second, the chimeric nature of the gene would provide multiple virus resistance. Third, nontranslatable construction produces no protein, thus reducing the possible complementation of naturally occurring mutants and transencapsidation of other viruses. Fourth, the small fragment also reduces the possibility of recombination with other viral genomes.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A DNA construct comprising in operable linkage:

a single promoter sequence;

a first DNA molecule which has a length that is insufficient to independently impart resistance to a virus to plants transformed with said first DNA molecule, wherein the first DNA molecule is from a DNA encoding a plant viral coat protein and is at least 110 nucleotides in length;

a second DNA molecule, wherein the second DNA molecule is coupled to the first DNA molecule, wherein said second DNA molecule is at least 400 nucleotides in length, wherein the first DNA molecule and the second DNA molecule are heterologous to each other and collectively achieve post-transcriptional silencing of the plant viral coat protein and impart resistance to the virus to plants transformed with said DNA construct; and wherein the single promoter sequence effects transcription of the first DNA molecule and the second DNA molecule; and a single termination sequence which ends transcription of the first DNA molecule and the second DNA molecule.

2. The DNA construct according to claim 1, wherein the first DNA molecule is from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, and tomato yellow leaf curl virus.

3. The DNA construct according to claim 1, wherein the second DNA molecule is selected from the group consisting of a viral cDNA molecule, a fluorescence protein encoding DNA molecule, and a combination. thereof 4. The DNA construct according to claim 1, wherein the first DNA molecule and the second DNA molecule encode RNA molecules which are translatable.

5. The DNA construct according to claim 1, wherein the first DNA molecule and the second DNA molecule encode RNA molecules which are non-translatable.

6. A DNA expression vector comprising the DNA construct of claim 1.

7. A host cell transformed with the DNA construct of claim 1.

8. A transgenic plant transformed with the DNA construct according to claim 1.

9. A method of increasing viral resistance to a plant comprising:

transforming a plant with a DNA construct according to claim 1, thereby resulting in a plant with increased resistance compared to an untransformed plant.

10. A transgenic plant seed comprising the DNA construct according to claim 1.

11. A method of increasing resistance to viral disease in a plant, wherein the method comprises:

planting a transgenic plant seed according to claim 10 and propagating a plant from the transgenic plant seed resulting in a plant with increased resistance to viral disease compared to an untransformed plant.

12. A DNA construct comprising in operable linkage:

a single promoter sequence which effects transcription of a plurality of DNA molecules;

a plurality of DNA molecules each of which is at least 110 nucleotides in length and at least one of which is of a length insufficient to impart resistance to a plant virus to plants transformed therewith and is from a DNA encoding a plant virus coat protein, wherein the plurality of DNA molecules collectively are at least 510 nucleotides in length, wherein the plurality of DNA molecules are heterologous to each other, and wherein the plurality of DNA molecules effect post-transcriptional silencing of the plant virus coat protein and impart resistance to the plant virus in plants transformed with the DNA construct; and a single termination sequence which ends transcription of the plurality of DNA molecules.

13. A DNA expression vector comprising the DNA construct of claim 12.

14. A host cell transformed with the DNA construct of claim 12.

15. A transgenic plant transformed with the DNA construct of claim 12.

16. A method of increasing viral resistance to plants comprising:

transforming the plant with a DNA construct according to claim 12, thereby resulting in a plant with increased resistance compared to an untransformed plant.

17. A transgenic plant seed comprising the DNA construct of claim 12.

18. A method of increasing viral resistance to plants, wherein the method comprises:

planting a transgenic plant seed according to claim 17 and propagating a plant from the trausgenic plant seed.

* * * * *